United States Patent [19]

Ikeda

[11] Patent Number: 5,354,852
[45] Date of Patent: Oct. 11, 1994

[54] POLYSACCHARIDE DERIVATIVE, PROCESS FOR PRODUCING THE SAME, AND SEPARATING AGENT

[75] Inventor: Hirokazu Ikeda, Hyogo, Japan

[73] Assignee: Daicel Chemical Industries, Ltd., Osaka, Japan

[21] Appl. No.: 940,951

[22] PCT Filed: Feb. 28, 1992

[86] PCT No.: PCT/JP92/00234

§ 371 Date: Oct. 27, 1992

§ 102(e) Date: Oct. 27, 1992

[87] PCT Pub. No.: WO92/15635

PCT Pub. Date: Sep. 17, 1992

[30] Foreign Application Priority Data

Mar. 4, 1991 [JP] Japan .................. 3-062653

[51] Int. Cl.$^5$ .................. C08B 37/00; C07H 1/00
[52] U.S. Cl. .................. 536/17.9; 536/53; 536/55.3; 536/124; 536/20; 536/56; 536/112
[58] Field of Search .................. 536/53, 56, 112, 124, 536/20, 21, 114, 1.11, 2, 3, 52, 55.3, 17.9

[56] References Cited

U.S. PATENT DOCUMENTS

| | | | |
|---|---|---|---|
| 4,861,872 | 8/1989 | Okamoto et al. | 536/20 |
| 4,912,205 | 3/1990 | Okamoto et al. | 536/20 |
| 5,026,841 | 6/1991 | Francotte et al. | 536/58 |
| 5,202,433 | 4/1993 | Okamoto et al. | 568/730 |

FOREIGN PATENT DOCUMENTS

| | | |
|---|---|---|
| 025639 | 3/1981 | European Pat. Off. |
| 157365 | 10/1985 | European Pat. Off. |
| 348352 | 12/1989 | European Pat. Off. |
| 63-060944 | 3/1988 | Japan . |

OTHER PUBLICATIONS

Database WPI, Week 8817, Derwent Publications Ltd.

*Primary Examiner*—Johnnie R. Brown
*Assistant Examiner*—Everett White
*Attorney, Agent, or Firm*—Flynn, Thiel, Boutell & Tanis

[57] ABSTRACT

A particulate aromatic or araliphatic carbamate of a polysaccharide having a mean particle diameter of 1 to 200 μm and a specific surface area of 0.5 to 300 m$_2$/g is prepared by first dissolving an aromatic or araliphatic carbamate of a polysaccharlde in an organic solvent, adding a hydrocarbon having 4 to 22 carbon atoms in an amount of 0 to 0.5 time by volume of that of the organic solvent, gradually adding the resultant solution to a sufficiently agitating aqueous surfactant solution, removing the organic solvent while continuing the agitation, isolating solid particles, and washing and drying the solid particles. The particulate aromatic or araliphatic carbamate of a polysaccharide has an excellent capability of resolution and, as such, can be used as a stationary phase of preparative liquid chromatography without being supported on a support.

5 Claims, No Drawings

POLYSACCHARIDE DERIVATIVE, PROCESS FOR PRODUCING THE SAME, AND SEPARATING AGENT

FIELD OF INDUSTRIAL APPLICATION

The present invention relates to a polysaccharide derivative, a process for producing the same, and a separating agent.

PRIOR ART

It is known that a packing material for liquid chromatography wherein use is made of a stationary phase comprising a silica gel and, supported thereon, an ester of a polysaccharide and a carbamate has an excellent capability of optical resolution (see Japanese Patent Publication-A No. 289601/1990 ). The silica gel used as a support, however, is very expensive. A process for producing a particulate cellulose ester of an aromatic or araliphatic carboxylic acid is well known in the art (see Japanese Patent Publication-A No. 152101/1989). However, a particulate aromatic or araliphatic carbamate of a polysaccharide has not been produced because the production thereof was difficult due to the limitation of the solubility and the solvent therefor.

DISCLOSURE OF THE INVENTION

The present inventors have made extensive studies with a view to solving the above-described problems and, as a result, have found that a particulate aromatic or araliphatic carbamate of a polysaccharide can be easily prepared, has an excellent capability of resolution because it is in the particulate form, particularly has a separation factor larger than that of the carbamate carried on a support, and is suitable for use in preparative liquid chromatography, thus accomplishing the present invention.

Accordingly, the present invention provides a polysaccharide derivative comprising a particulate aromatic or araliphatic carbamate of a polysaccharide having a mean particle diameter of 1 to 200 μm and a specific surface area of 0.5 to 300 m²/g, a process for producing the same, and a separating agent comprising said polysaccharide derivative for use in the separation of racemic compounds and structural isomer mixtures, particularly a separating agent for use as a stationary phase in chromatography.

In the present invention, the mean particle diameter of the polysaccharide derivative is 1 to 200 μm, although it depends upon the application, preferably 3 to 20 μm for analytic applications and 10 to 200 μm for preparative applications. It is possible to attain a very narrow mean particle diameter range by fractionation through the use of a conventional method, for example, sedimentation, sifting or centrifugation by means of a cyclone.

The specific surface area of the polysaccharide derivative according to the present invention is 0.5 to 300 m²/g, preferably 1 to 80 m²/g. The particle is spherical or crushed in its shape, preferably spherical. The surface of the particle may be porous or non-porous, preferably porous for the purpose of increasing the absorption area and improving the performance of separation. The particle diameter distribution is preferably narrow when the particle is used as a separating agent for chromatography.

The aromatic or araliphatic carbamate of a polysaccharide of the present invention is derived from an Isocyanate represented by the following formulas (1) or (2):

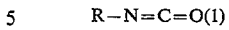

$$R-N=C=O \quad (1)$$

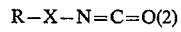

$$R-X-N=C=O \quad (2)$$

(wherein R stands for a monovalent aromatic hydrocarbon group which may have a heteroatom and may be unsubstituted or substituted with at least one member selected from the group consisting of a hydrocarbon group having 1 to 12 carbon atoms and optionally a heteroatom, a cyano group, a halogen atom, a hydroxy group, a nitro group, an amino group and a di($C_1$ to $C_8$ alkyl) amino group; and X stands for a divalent hydrocarbon group which has 1 to 4 carbon atoms and which may have a double bond or a triple bond).

Examples of the monovalent aromatic hydrocarbon group represented by the R include groups such as phenyl, naphthyl, phenanthryl, anthracyl, indenyl, indanyl, furyl, thionyl, pyrryl, benzofuryl, benzthionyl, indyl, pyridyl, pyrimidyl, quinolinyl and isoquinolinyl.

Examples of the substituents of the monovalent aromatic hydrocarbon group represented by the R include an alkyl group having 1 to 12 carbon atoms, an alkoxy group having 1 to 12 carbon atoms, an alkylthio group having 1 to 12 carbon atoms, a cyano group, a halogen atom, an acyl group having 1 to 8 carbon atoms, an acyloxy group having 1 to 8 carbon atoms, a hydroxy group, an alkoxycarbonyl group having 1 to 12 carbon atoms, a nitro group, an amino group and a di($C_1$ to $C_8$ alkyl)amino group.

X is a divalent hydrocarbon group having 1 to 4 carbon atoms and may have a double bond or a triple bond. Examples of X include methylene, ethylene, ethylidene, ethenylene, ethynylene, 1,2-or 1,3-propylene and 1,1- or 2,2-propylidene.

In the present invention, although the polysaccharide may be any of naturally occurring polysaccharides, synthetic polysaccharides and naturally occurring modified polysaccharides as far as they are optically active, it is preferably a polysaccharide having a highly regular bonding form. Examples of the polysaccharide include β-1,4-glucan (cellulose ), α-1,4-glucan (amylose, aminopectin or cyclodextrin), α-1,6-glucan (dextran), β-1,6-glucan (pustulan), β-1,3-glucan (for example, curdlan, schizophyllan or the like), α-1,3-glucan, β-1,2-glucan (crown gall polysaccharide ), β-1,4-galactan, β-1,4mannan, α-1,6-mannan, β-1,2-fructan (inulin), β-2,6fractan (levan), β-1,4-xylan, β-1,3-xylan, β-1,4chitosan, β-1,4-N-acetylchitosan (chitin), pullulan, agarose and alginic acid, and still preferred examples of the polysaccharide include cellulose, amylose, β-1,4-chitosan, β-1,4-mannan, β-1,4-xylan, inulin, chitin, chitosan and curdlan which enable polysaccharides having a high purity to be easily prepared. The number-average degree of polymerization of the polysaccharide (the average number of the pyranose or furanose rings contained in its molecule) is 5 or more, preferably 10 or more. Although the upper limit of the number-average degree of polymerization is not crucial, the upper limit is preferably 500 or less from the viewpoint of handleability.

The aromatic or araliphatic carbamate of a polysaccharide to be used in the present invention can be produced from an Isocyanate represented by the formulas (1) or (2) and a polysaccharlde by a conventional method.

The percentage introduction of the substituent of the polysaccharlde is 10 to 100%, preferably 80 to 100%.

The particulate aromatic or araliphatic carbamate of a polysaccharide having a mean particle diameter of 1 to 200/μm and a specific surface area of 0.5 to 300 m²/g according to the present invention can be prepared by first dissolving an aromatic or araliphatic carbamate of a polysaccharide in an organic solvent, adding a hydrocarbon having 4 to 22 carbon atoms in an amount of 0 to 0.5 by volume of that of the organic solvent, gradually adding the resultant solution to a sufficiently agitated aqueous surfactant solution, removing the organic solvent while continuing the agitation, isolating solid particles, and washing and drying the solid particles.

In the above-described method, the particle diameter of the resultant polysaccharlde derivative varies depending upon the ratio of the amount of the organic solvent to the amount of the aqueous solution, the concentration of the polysaccharlde derivative, the rate of addition of the organic solvent, and the shapes of the vessel and the stirring blade, when the agitation rate is 10 to 1000 rpm, preferably 100 to 500 rpm.

Although the organic solvent is not particularly limited as far as it can dissolve the polysaccharide carbamate, an organic solvent which is insoluble in water is particularly preferred. Even if the organic solvent is one which is soluble in water, it can be used after being mixed with an solvent which is insoluble in water.

The amount of the hydrocarbon to be added to a solution of a polysaccharide derivative in an organic solvent is 0 to 0.5 by volume, preferably 0.1 to 0.3 by volume of that of the organic solvent. The number of carbon atoms of the hydrocarbon is 2 to 22, preferably 4 to 10. Examples of the hydrocarbon include butane, pentane, heptane, hexane, octane, nonane and decane.

The ratio of the total volume of the organic solvent, polysaccharlde derivative and hydrocarbon to that of the aqueous surfactant solution is preferably 1 : 10 to 1 : 1.

In the present invention, the term "surfactant" refers to an acid, a dibasic acid, a tribasic acid, a tetrabasic acid or a hemlester or salt thereof, preferably an alkyl sulfate having 4 to 18 carbon atoms, particularly preferably a lauryl sulfate.

The particulate polysaccharlde derivative thus prepared according to the present invention is useful as a separating agent for separating a racemic mixture, a structural isomer mixture, particularly as a packing material for gas chromatography and liquid chromatography.

EFFECT OF THE INVENTION

The polysaccharide derivative of the present invention is very useful as functional material, particularly useful for separating a racemic mixture and a structural isomer mixture. Since the polysaccharide derivative of the present invention is particulate, it is not necessary to use an expensive supporting material (silica gel) and it can be produced in a large quantity at a low cost. Further, when the surface of the particle is made porous, the separation factor can be increased through an increase in the specific surface area of the particle, which enables the separation to be conducted at a high efficiency and a high profitability.

EXAMPLES

The present invention will now be described in more detail with reference to the following Examples, though it is not limited to these Examples only.

EXAMPLE 1

8.7 g of cellulose-3,5-dimethylphenylcarbamate was dissolved in 300 ml of mesityl oxide. The resultant solution was gradually added in portions to 600 ml of a 0.75% aqueous sodium lauryl sulfate solution being agitated at about 400 rpm. The reaction system was heated to 90° C. and evacuated while continuing the agitation at the same rate. 250 ml of distilled water was added in the course of the above procedure to distill away mesityl oxide. The residue was isolated by filtration and washed with distilled water and ethanol. The resultant powder was dried in vacuo at 140° C. for 16 hr. The yield of the resultant powder was 8.1 g (93%). The powder was classified by sifting and sedimentation to prepare a spherical particle having a diameter of 3 to 6 μm and a specific surface area of 3.4 m²/g (BET method).

EXAMPLE 2

The powder prepared In the Example 1 was packed in a column having an inner diameter of 4.6 mm and a length of 125 mm, and the separation of various racemic compounds listed in Table 1 was conducted by HPLC. The results are given in Table 1.

EXAMPLE 3

10.0 g of cellulose-3,5-dlmethylphenylcarbamate was dissolved in a mixed solvent comprising 250 ml of mesityl oxide and 50 ml of acetone, and 50 ml of n-nonane was added thereto. The resultant solution was gradually added in portions to 600 ml of a 0.75% aqueous sodium lauryl sulfate solution being agitated at about 400 rpm. The reaction system was heated to 90° C. and evacuated while continuing the agitation at the same rate. 200 ml of distilled water was added in the course of the above procedure to distil away mestyl oxide and acetone. The residue was isolated by filtration and washed with distilled water and ethanol. The resultant powder was dried in vacuo at 140° C. for 16 hr. The yield of the resultant powder was 7.83 g (78.3%). The powder was classified by sifting and sedimentation to prepare a spherical particle having a diameter of 3 to 8 μm and a specific surface area of 4.8 m²/g (BET method).

EXAMPLE 4

The powder prepared in Example 3 was packed in a column having an inner diameter of 4.6 mm and a length of 100 mm, and the separation of various racemic compounds listed in Table 1 was conducted by HPLC. The results are given in Table 1.

EXAMPLE 5

10.0 g of cellulose-3,5-dlmethylphenylcarbamate was dissolved in a mixed solvent comprising 250 ml of mesityl oxide and 50 ml of acetone, and 50 ml of n-nonane was added thereto. The resultant solution was gradually added in portions to 600 ml of a 0.75% aqueous sodium lauryl sulfate solution being agitated at about 200 rpm. The reaction system was heated to 90° C. and evacuated while continuing the agitation at the same rate. 200 ml of distilled water was added in the course of the above procedure to distil away mesityl oxide and acetone. The residue was isolated by filtration and washed with distilled water and ethanol. The resultant powder was dried in vacuo at 140° C. for 16 hr. The yield of the resultant powder was 8.46 g (84.6%). The powder was classified by sifting and sedimentation to prepare a spherical particle having a diameter of 12 to 30 μm and a specific surface area of 1.2 m²/g (BET method).

EXAMPLE 6

10.0 g of amylose-3,5-dlmethylphenylcarbamate was dissolved in a mixed solvent comprising 300 ml of chloroform and 6 ml of N,N-dimethylacetamide, and 40 ml of n-heptane was added thereto. The resultant solution was gradually added in portions to 600 ml of a 0.75% aqueous sodium lauryl sulfate solution being agitated at about 400 rpm. The reaction system was heated to 60° C. and evacuated while continuing the agitation at the same rate to distil away the organic solvent. The residue was isolated by filtration and washed with distilled water and ethanol. The resultant powder was dried in vacuo at 90° C. for 20 hr. The yield of the resultant powder was 9.41 g (94.1%). The powder was classified by sifting and sedimentation to prepare a spherical particle having a diameter of 3 to 6 μm and a specific surface area of 4.3 m²/g (BET method).

EXAMPLE 7

The powder prepared in Example 6 was packed in a column having an inner diameter of 4.6 mm and a length of 125 mm, and the separation of various racemic compounds listed in Table 1 was conducted by HPLC. The results are given in Table 1.

TABLE 1

| racemic compd. | Ex. 2 | | Ex. 4 | | Ex. 7 | |
| --- | --- | --- | --- | --- | --- | --- |
| | $k_1'$ | α | $k_1'$ | α | $k_1'$ | α |
| t-stilbene oxide | 5.41 | 1.76 | 1.20 | 2.64 | 1.76 | 2.92 |
| Tröger's base | 7.15 | 1.28 | 1.84 | 1.21 | 1.82 | 1.69 |
| benzoin | 15.19 | 1.58 | 3.61 | 1.69 | 12.95 | 1.32 |
| phenyl vinyl sulfoxide | 12.89 | 1.25 | 2.69 | 1.41 | 4.93 | 1.0 |
| trifluoroanthryl-ethanol | 15.76 | 2.47 | 2.97 | 3.52 | 4.63 | 1.39 | mobile phase: hexane/2-propanol=9/1
flow rate: 0.5 ml/min
temp.: room temp.
The HPLC used was one (pump: 880-PU, detector: 875-UV) manufactured by Japan Spectroscopic Co., Ltd.

In the table, the volumetric ratio ($k_1'$) and the separation factor (α) are defined by the following equations:

$$\text{volumetric ratio } (k_1') = \frac{\text{retention time of separating compd.} - \text{dead time}}{\text{dead time}}$$

$$\text{separation factor } (\alpha) = \frac{\text{volumetric ratio of more strongly adsorbed compd.}}{\text{volumetric ratio of more weakly adsorbed compd.}}$$

EXAMPLE 8

10 g of cellulose tris(phenylcarbamate) was dissolved in a mixed solvent comprising 250 ml of mesityl oxide and 50 ml of acetone, and 50 ml of n-nonane was added thereto. The mixture was agitated until the opaque solution turned transparent. The solution was gradually added in portions to 600 ml of a 0.75% aqueous sodium lauryl sulfate solution being agitated at about 400 rpm. The reaction system was heated to 40° C. and evacuated while continuing the agitation at the same rate to distil away the organic solvent. The residue was isolated by filtration and washed with distilled water and ethanol. The resultant powder was dried in vacuo at 140° C. for 19 hr. The yield of the resultant powder was 7.2 g (72%). The powder was classified by sifting and sedimentation to prepare a spherical particle having a diameter of 6 to 15 μm and a specific surface area of 5.4 m²/g (BET method).

EXAMPLE 9

The powder prepared in Example 8 was packed in a column having an inner diameter of 4.6 mm and a length of 125 mm, and the separation of various racemic compounds listed in Table 2 was conducted by HPLC. The results are given in Table 2.

TABLE 2

| | Ex. 9 | |
| --- | --- | --- |
| racemic compd. | $k_1'$ | α |
| t-stilbene oxide | 6.13 | 1.40 |
| phenyl vinyl sulfoxide | 58.32 | 1.15 |
| 2,2,2-trifluoro-1-(9-anthryl)-ethanol | 9.95 | 1.36 | mobile phase: hexane/2-propanol=9/1
flow rate: 0.5 ml/min
temp.: room temp.
The HPLC used was one (pump: 880-PU, detector: 875-UV) manufactured by Japan Spectroscopic Co., Ltd.

EXAMPLE 10

10 g of cellulose tris(phenylcarbamate) was dissolved in a mixed solvent comprising 250 ml of methylene oxide and 10 ml of acetone, and the resultant solution was gradually added in portions to 600 ml of a 0.75% aqueous sodium lauryl sulfate solution being agitated at about 400 rpm. The reaction system was heated to 45° C. while continuing the agitation at the same rate to distil away the organic solvent. The residue was isolated by filtration and washed with distilled water and ethanol. The resultant powder was dried in vacuo at 80° C. for 20 hr. The yield of the resultant powder was 9.4 g (94%). The powder was classified by sifting and sedimentation to prepare a spherical particle having a diameter of 10 to 30 μm.

I claim:

1. Spherical particles of an aromatic or araliphatic carbamate of a polysaccharide having a mean particle diameter of 1 to 200 μm and a specific surface area of 0.5 to 300 m²/g.

2. Spherical particles according to claim 1, wherein said aromatic or araliphatic carbamate of a polysaccharide is a compound derived from an isocyanate represented by the following formulas (1) or (2):

$$R-N=C=O \qquad (1)$$

$$R-X-N=C=O \qquad (2)$$

wherein R stands for a monovalent aromatic hydrocarbon group which may have a heteroatom and may be unsubstltuted or substituted with at least one member selected from the group consisting of a hydrocarbon group having 1 to 12 carbon atoms and optionally a heteroatom, a cyano group, a halogen atom, a hydroxy group, a nltro group, an amino group and a di($C_1$ to $C_8$ alkyl )amino group; and X stands for a dlvalent hydrocarbon group which has 1 to 4 carbon atoms and may have a double bond or a triple bond.

3. A process for producing spherical particles of an aromatic or araliphatic carbamate of a polysaccharide having a mean particle diameter of 1 to 200 μm and a specific surface area of 0.5 to 300 m²/g, said process comprising the steps of first dissolving an aromatic or araliphatic carbamate of a polysaccharide in an organic solvent, adding a hydrocarbon having 4 to 22 carbon atoms in an amount of 0 to 0.5 time by volume of that of the organic solvent to form a resultant solution, gradually adding the resultant solution to a sufficiently agitated aqueous surfactant solution, removing the organic solvent while continuing the agitation, isolating formed solid spherical particles, and washing and drying the solid particles.

4. The process according to claim 3, wherein the organic solvent has a mesityl oxide content of 50 to 100% by volume.

5. In a process of separating racemic compounds or structural isomer mixtures, the improvement comprising contacting said racemic compounds or structural isomer mixtures with a separating agent comprising spherical particles of an aromatic or araliphatic carbamate of a polysaccharide having a mean particle diameter of 1 to 200 μm and a specific surface area of 0.5 to 300 m²/g.

* * * * *

UNITED STATES PATENT AND TRADEMARK OFFICE
CERTIFICATE OF CORRECTION

PATENT NO. : 5 354 852
DATED : October 11, 1994
INVENTOR(S) : Hirokazu IKEDA

It is certified that error appears in the above-indentified patent and that said Letters Patent is hereby corrected as shown below:

```
Column 6, line 68;   replace "unsubstltuted" with
                     ---unsubstituted---.
Column 7, line 4;    replace "nltro" with ---nitro---.
         line 6;     replace "dlvalent" with ---divalent---.
```

Signed and Sealed this

Fourteenth Day of March, 1995

Attest:

BRUCE LEHMAN

Attesting Officer   Commissioner of Patents and Trademarks